(12) United States Patent
Ando et al.

(10) Patent No.: US 7,534,598 B2
(45) Date of Patent: May 19, 2009

(54) APPARATUS AND METHOD FOR INJECTING SUBSTANCE INTO CELL

(75) Inventors: Moritoshi Ando, Kawasaki (JP); Satoru Sakai, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 631 days.

(21) Appl. No.: 11/067,351

(22) Filed: Feb. 28, 2005

(65) Prior Publication Data
US 2005/0277182 A1  Dec. 15, 2005

(30) Foreign Application Priority Data
Jun. 15, 2004  (JP) .............................. 2004-177197

(51) Int. Cl.
*C12M 1/42* (2006.01)
*C12N 15/89* (2006.01)

(52) U.S. Cl. .................. 435/285.1; 435/173.5; 435/460

(58) Field of Classification Search .............. 435/173.5, 435/173.7, 285.1, 285.2, 287.1, 460
See application file for complete search history.

(56) References Cited

U.S. PATENT DOCUMENTS

| | | | |
|---|---|---|---|
| 5,702,384 A | 12/1997 | Umeyama et al. | |
| 6,368,851 B1 * | 4/2002 | Baumann et al. | 435/285.2 |
| 7,320,885 B1 * | 1/2008 | Saito | 435/173.5 |
| 2002/0142465 A1 | 10/2002 | Kobayashi et al. | |

FOREIGN PATENT DOCUMENTS

| | | |
|---|---|---|
| DE | 3707111 | 9/1988 |
| EP | 1211307 | 6/2002 |
| JP | 61-194335 | 8/1986 |
| JP | 02186993 | 7/1990 |
| JP | 5-300946 | 11/1993 |
| JP | 8-290377 | 11/1996 |
| JP | 2002-281970 | 10/2002 |
| JP | 2003-70468 | 3/2003 |
| JP | 2003070468 | 11/2003 |
| WO | 00/34436 | 6/2000 |
| WO | WO 01/19953 | 3/2001 |

OTHER PUBLICATIONS

EP Search Report for corresponding application EP 05251179.7 dated Oct. 6, 2005.
Palumbo, G. et al., "Targeted Gene Transfer in Eucaryotic Cells by Dye-Assisted Laser Optoporation", Journal of Photochemistry and Photobiology B: Biology, Elsevier Sciences S.A., Basel, CH, vol. 36, 1996, pp. 41-46.

* cited by examiner

*Primary Examiner*—William H Beisner
(74) *Attorney, Agent, or Firm*—Fujitsu Patent Center

(57) ABSTRACT

A surface of a cell is irradiated with laser beam to make an opening in the cell membrane, and a drug fluid is inserted in the cell through the opening.

7 Claims, 14 Drawing Sheets

APPARATUS AND METHOD FOR INJECTING SUBSTANCE INTO CELL

BACKGROUND OF THE INVENTION

1) Field of the Invention

The present invention relates to an apparatus and method for injecting a substance into cells.

2) Description of the Related Art

To modify the characteristics of the cells it is common to inject genes or drugs into cells in the field of life science, particularly regeneration medicine and genome drug discovery. With such a technology, roles of genes can be made clear and tailor made medicines that perform gene therapy suited for genetic characteristics of an individual can be prescribed.

Various methods have been proposed for injecting liquids into the cells to produce genetically modified cells. These methods include electrical methods, chemical methods, mechanical methods, and optical methods. The electropolation method is an example of the electrical method. The lipofection method is an example of the chemical method. The microinjection method is an example of the mechanical method. The laser injection method is an example of the optical method.

Among these, the electropolation method includes puncturing a cell membrane with electric pulses to form a hole in the cell membrane and injecting a drug fluid through the hole. This method can be used for any combination of cells and drug fluids. However, it is difficult to accurately control the puncturing of the cell. For example, the cell membrane may not be punctured successfully or, conversely, the cell membrane is punctured to the extent that the cells may die. There is also a problem that the ratio of successful introduction of the substance in the cell is very low.

The lipofection method involves mixing charged liposomes with DNA and allowing the resultant to adsorb onto the surface of cells so that the DNA enters into the cells. The virus vector method includes incorporating a gene into a virus DNA to prepare a genetic recombinant virus, and introducing the gene into the cells with the mechanism of the infection of the genetic recombinant virus.

However, the chemical and biological methods can be applied only to the limited combinations of the cells and the substances. In particular, in the case of the virus vector method, the risk of causing infectious diseases is relatively high since the method uses cells that have a high infectious capacity.

The microinjection method includes filling a drug fluid in a fine needle of diameter 1 micrometer (μm) and jabbing the needle into a cell and injecting the drug fluid in the cell (see, for example, Japanese Patent Application Laid-Open Publication No. H08-290377). FIG. 21 is a schematic for explaining a method for injecting a drug fluid into cells by the microinjection method. A needle 1 that holds a drug fluid 2 is jabbed into a cell membrane of a cell 3, and a pressure is applied to the drug fluid 2 so that the drug fluid 2 is injected into the cell 3 in the direction toward a nucleus 4 of the cell 3.

The tip of the needle 1 has a high surface tension because it is very thin, therefore, the drug fluid 2 is difficult to be led to the tip. One approach is to insert a glass rod 5 inside the needle 1. The presence of the glass rod 5 breaks the balance of the surface tension at an acute angle portion formed between the glass rod 5 and an inside of the needle 1, allowing the drug fluid 2 to be led to the tip of the needle 1.

The laser injection method involves dissolving a drug in a culture fluid for culturing cells and irradiating a laser beam to the cell membranes of the cells to form an opening in the cell membranes without using any needle. FIG. 22 is a schematic for explaining a method for injecting a drug fluid by the laser injection method. The drug fluid 2 is caused to penetrate into a cell 7 by the Brownian motion through an opening that is formed by the irradiation of a laser 6 to the cell 7 (see, for example, Japanese Patent Application Laid-Open Publication No. 2003-70468).

In the conventional microinjection method, if the same needle is used repeatedly, pieces of the cell membrane stick to the needle or enter into the needle. The pieces of the cell membrane that stick to the needle make the tip of the needle thicker. The pieces of the cell membrane that enter into the needle clog the tip. These situations make the injection difficult. Accordingly, it becomes necessary to periodically exchange the needle with a new one.

On the other hand, in the conventional laser injection method, it is necessary to make the laser beam very thin to precisely control the irradiation position of the laser so as not to damage the cells. For this purpose, it becomes necessary to observe the cells through a high magnification objective lens, which decreases the efficiency of the method.

The drug fluid is expensive and cannot be used in large amounts. This makes it necessary to use a smaller vessel to charge the cells to avoid a decrease in the concentration of the drug fluid. Accordingly, when the drug fluid is to be injected into a lot of cells, the operation of injecting the drug fluid into the cells and the operation of recovering the injected cells must be performed, for example, by charging the cells in separate vessels, respectively, one for one. This further decreases the efficiency of the conventional methods.

SUMMARY OF THE INVENTION

It is an object of the present invention to solve at least the problems in the conventional technology.

According to an aspect of a present invention, an apparatus for injecting a substance into a cell includes a light conducting unit that conducts a laser beam to a surface of a cell whereby an opening is formed in the surface; and a substance injecting unit that inserts the substance into the cell through the opening.

According to another aspect of a present invention, a method for injecting a substance into a cell includes irradiating a surface of a cell with a laser beam to form an opening in the surface of the cell; and inserting the substance into the cell through the opening.

The other objects, features, and advantages of the present invention are specifically set forth in or will become apparent from the following detailed description of the invention when read in conjunction with the accompanying drawings.

DETAILED DESCRIPTION

Exemplary embodiments of the present invention are explained in detail below with reference to the accompanying drawings. An apparatus and method for injecting a drug fluid into cells in a culture fluid are explained below as an example of the present invention.

Figure 1:
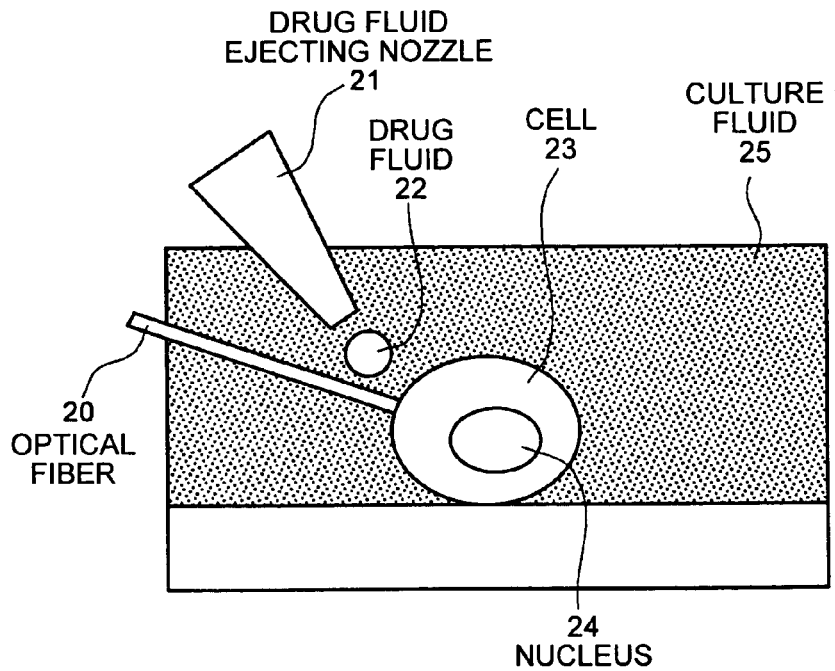
FIG. 1 is a schematic of an exemplary configuration of a drug fluid injecting section that can be used in a drug fluid injecting apparatus according to a first embodiment.
Figure 2:
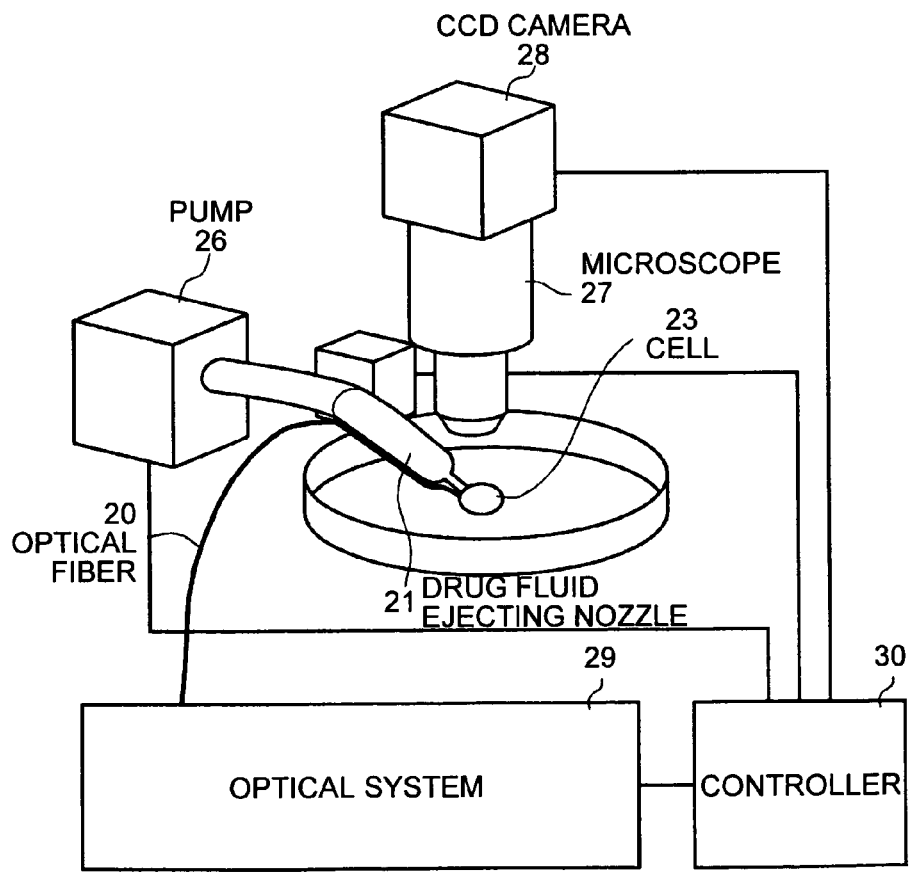
FIG. 2 is a schematic of the drug fluid injecting apparatus according to the first embodiment.

FIG. 1 is a schematic of an exemplary configuration of a drug fluid injecting section that can be used in a drug fluid injecting apparatus according to the first embodiment of the present invention. FIG. 2 is a schematic of the drug fluid injecting apparatus according to the first embodiment. The drug fluid injecting section of the drug fluid injecting apparatus includes an optical fiber 20 and a drug fluid ejecting nozzle 21.

The optical fiber 20 conducts a high power laser to a cell 23 immersed in a culture fluid 25 to form an opening in a cell membrane of the cell 23. The tip of the optical fiber 20 points toward a nucleus 24 of the cell 23. When the laser falls on the cell membrane, the cell membrane absorbs the laser so that the temperature of that portion of the surface of the cell increases. The heat due to the rise in the temperature causes the portion to melt thereby forming an opening in the cell membrane.

Examples of the laser that can be used include high power infrared pulse lasers such as an Ne:YAG laser and a Ti:Sapphire laser. Ar gas lasers and semiconductor lasers can also be used.

The drug fluid ejecting nozzle 21 ejects the drug fluid 22 into the inside of the cell 23 through the opening in the cell 23 formed by the laser conducted through the optical fiber 20. The direction in which the drug fluid ejecting nozzle 21 ejects the drug fluid 22 is adjusted to be directed toward the tip of the optical fiber 20 to which an opening is to be formed. Since the opening is formed by the irradiation of a laser beam, the tip of the nozzle 21 can be thicker than that of the needle in the conventional microinjection method.

While the laser is irradiated and the drug fluid 22 is injected, the cell 23 is fixed to a vessel, such as a Petri dish, with an adhesive suited for cells. As will be explained later, the cell 23 may be fixed by trapping the cell 23 in a hole by sucking the culture fluid.

The laser is conducted to just near a surface of the cell 23 through the optical fiber 20 and irradiated to form an opening in the cell membrane, and the drug fluid 22 is injected through the opening. This avoids the necessity of using a needle as in the conventional microinjection method and makes the control of the irradiation of the laser easier than the conventional laser injection method. Accordingly, injection of the drug fluid 22 can be performed at low cost and efficiently.

The drug fluid 22 to be injected into the cell 23 is stored in the inside of the drug fluid ejecting nozzle 21, so that dilution with the culture fluid can be prevented and the drug fluid injecting process can be performed with a small amount of the drug fluid 22.

As shown in FIG. 2, the drug fluid injecting apparatus includes the optical fiber 20, the drug fluid ejecting nozzle 21, a pump 26, a microscope 27, a Charge Coupled Device (CCD) camera 28, an optical system 29, and a controller 30.

The pump 26 applies a pressure to the drug fluid 22 when the drug fluid 22 is ejected from the drug fluid ejecting nozzle 21. The microscope 27 is an optical microscope with which the position of the cell 23 is observed. The CCD camera 28 captures an image of the cell (hereafter, "cell image") through the microscope 27. The cell image is transmitted to a personal computer (not shown) where the image is analyzed.

Figure 3:
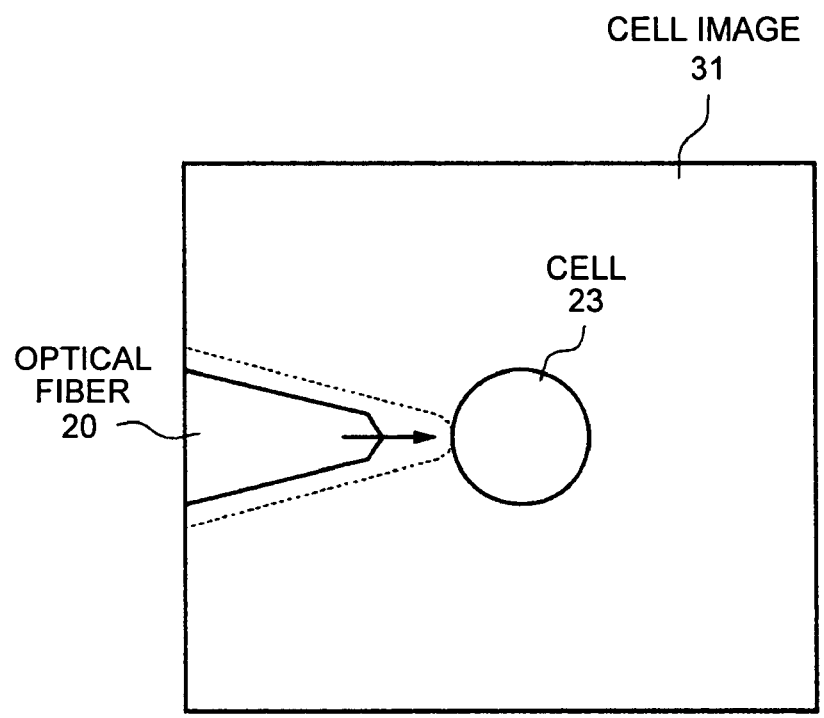
FIG. 3 is an example of a cell image taken by a CCD camera shown in FIG. 2.

FIG. 3 is an example of a cell image 31 taken by the CCD camera 28. The cell image 31 includes the cell 23 and the tip of the optical fiber 20. The personal computer can calculate, for example, a distance between the tip of the optical fiber 20 and the cell 23 by analyzing the cell image 31.

Referring to FIG. 2 again, the optical system 29 generates a high-power pulse laser that forms an opening in the cell 23. The optical system 29 also generates a low-power continuous wave (CW) laser having a different wavelength than that of the pulse laser. The wavelength of the CW laser suited for the cells 23 is in the range of red, infrared, and so on.

Figure 4:
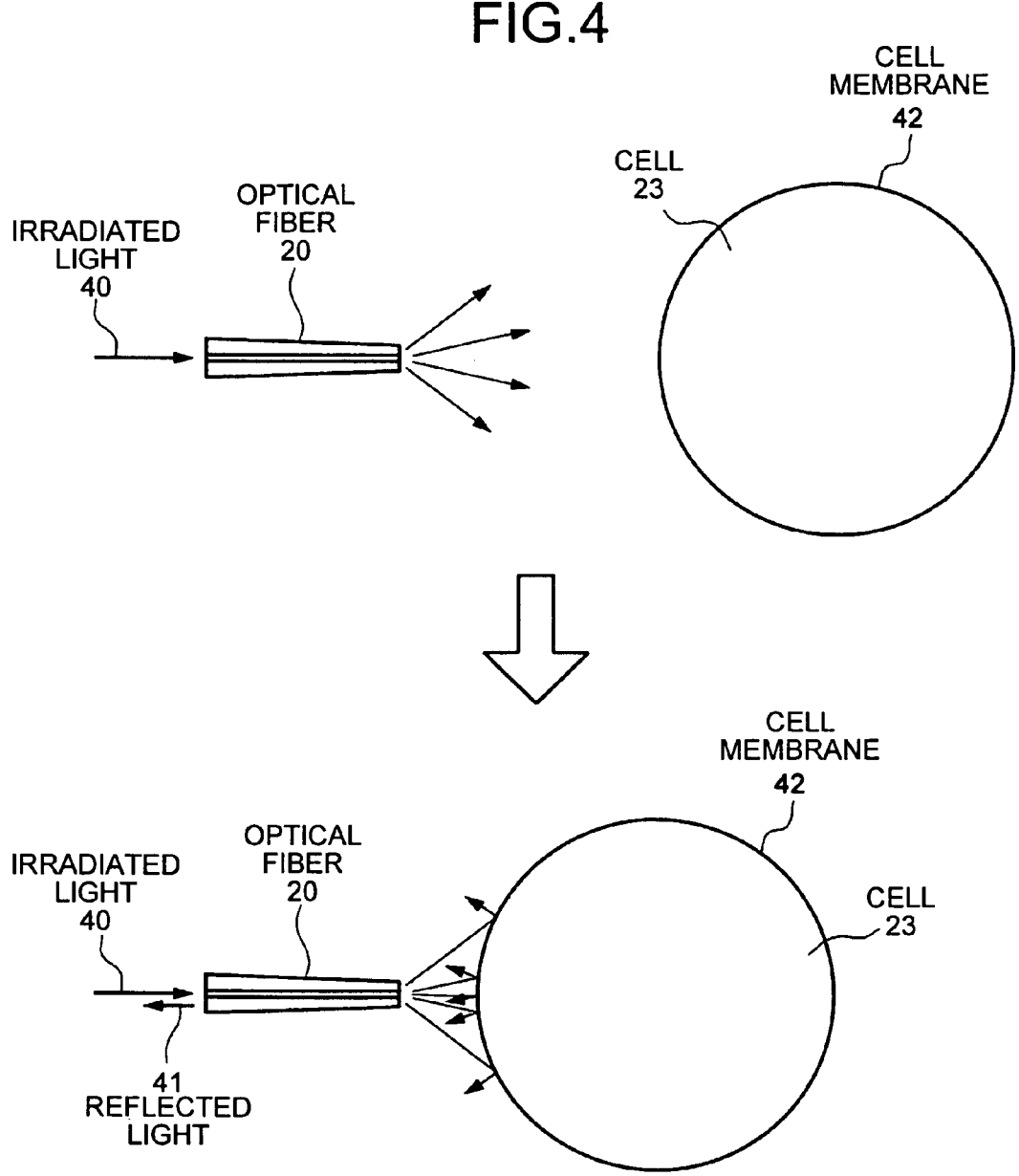
FIG. 4 is a schematic for explaining a method for determining the distance between the tip of an optical fiber shown in FIG. 1 and a cell.

FIG. 4 is a schematic for explaining a method for determining the distance between the tip of the optical fiber 20 and the cell 23. An irradiated light 40, which is the CW laser generated by the optical system 29, is irradiated to the cell 23 through the optical fiber 20.

The irradiated light 40 that is irradiated to the cell 23 is reflected by a cell membrane 42. As the tip of the optical fiber 20 approaches the cell 23, the intensity of reflected light 41 that passes through the inside of the optical fiber 20 and returns increases. Accordingly, the distance between the tip of the optical fiber 20 and the cell 23 can be calculated by measuring the intensity of the reflected light.

Figure 5:
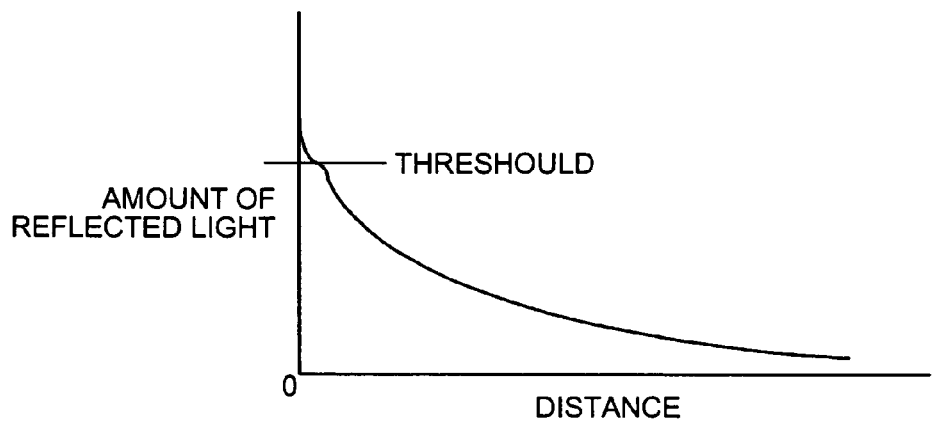
FIG. 5 is a graph of the intensity of reflected light verses the distance between an optical fiber and a cell shown in FIG. 4.

FIG. 5 is a graph of the intensity of the reflected light 41 verses the distance between the optical fiber 20 and the cell 23. The intensity of the reflected light 41 (amount of reflected light) decreases with the distance between the optical fiber 20 and the cell 23.

By preliminarily examining a threshold of the amount of reflected light when the tip of the optical fiber 20 contacts the cell 23 and detecting whether the actual amount of reflected light to reach the threshold, the timing when an opening is formed in the cell membrane and the drug fluid 22 is ejected therethrough can be appropriately judged.

Figure 6:
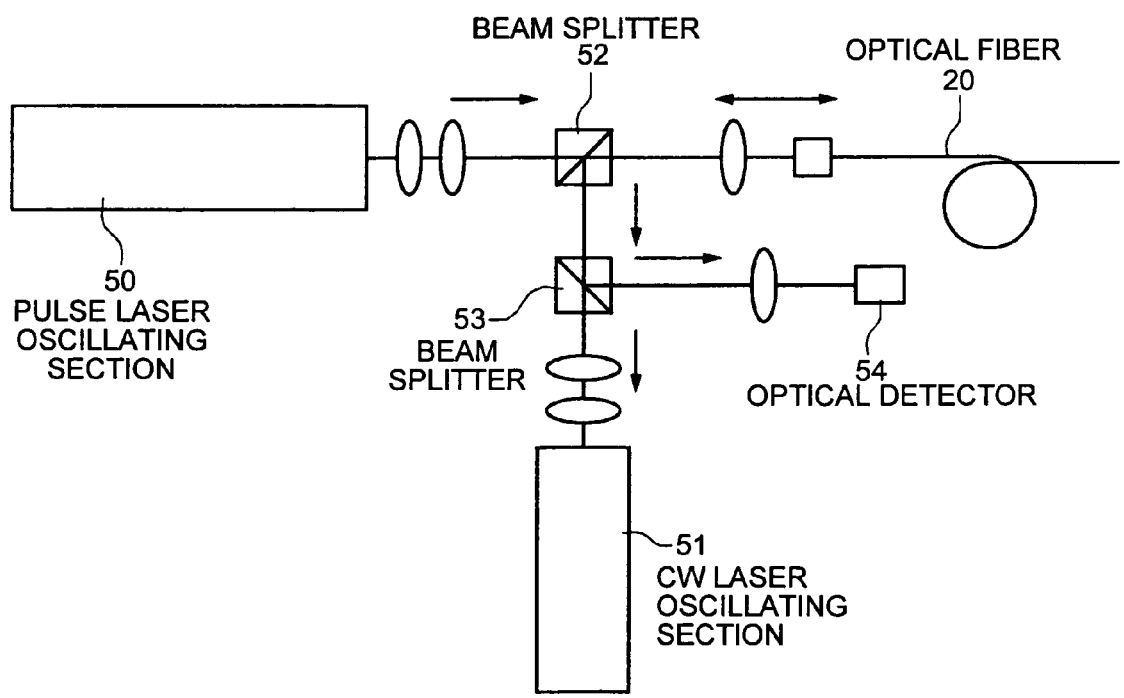
FIG. 6 is a detailed configuration of an optical system shown in FIG. 2.

FIG. 6 is a detailed configuration of the optical system 29 shown in FIG. 2. The optical system 29 includes a pulse laser oscillating section 50, a CW laser oscillating section 51, a beam splitter 52, a beam splitter 53, and an optical detector 54.

The pulse laser oscillating section 50 oscillates a high-power pulse laser that forms an opening in the cell membrane of the cell 23. The CW laser oscillating section 51 oscillates a CW laser for measuring the distance between the cell 23 and the tip of the optical fiber 20. The beam splitters 52 and 53 introduce the pulse laser and CW laser oscillated by the pulse laser oscillating section 50 and the CW laser oscillating section 51, respectively, into the optical fiber 20 and conduct the reflected light 41 that is reflected by the cell to return to the optical detector 54.

The optical detector 54 judges the timing in which an opening is formed and the drug fluid 22 is ejected, based on the relationship between the intensity of reflected light of the CW laser and the distance between the tip of the optical fiber 20 and the cell 23 as shown in FIG. 5. Specifically, the optical detector 54 outputs a signal that requests oscillation of a pulse laser to the pulse laser oscillating section 50 when the amount of reflected light of the reflected light 41 exceeds the predetermined threshold as shown in FIG. 5.

Referring to FIG. 2 again, the controller 30 controls the whole the drug fluid injecting apparatus. More particularly, the controller 30 controls the pump 26, the microscope 27, the CCD camera 28, and the optical system 29 to realize the drug fluid injection process.

Figure 7:
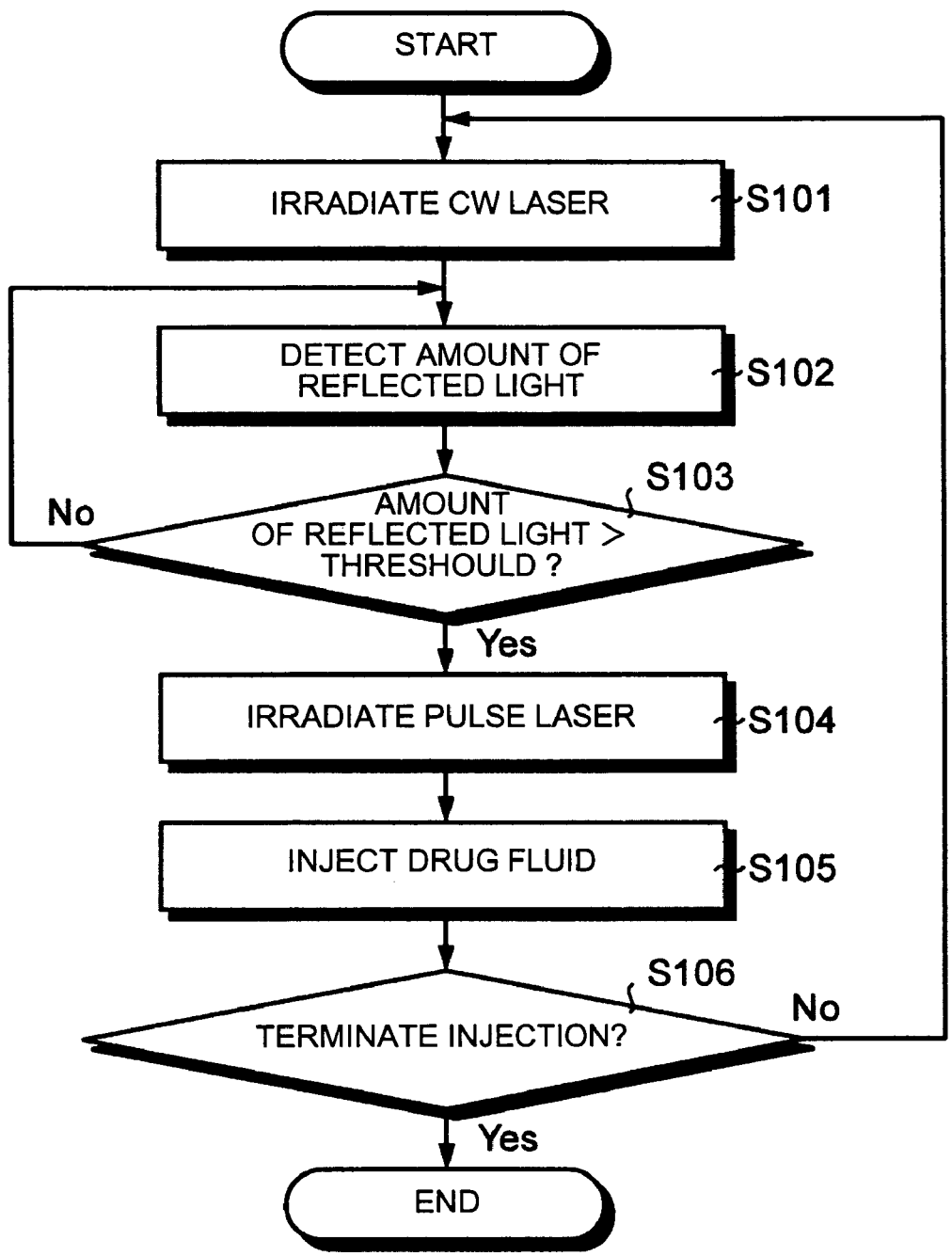
FIG. 7 is a flowchart of a drug fluid injecting process performed by the drug fluid injecting apparatus shown in FIG. 1.

Then, a drug fluid injection process performed by the drug fluid injecting apparatus according to the first embodiment is explained. FIG. 7 is a flowchart of the drug fluid injecting process performed by the drug fluid injecting apparatus shown in FIG. 2.

First, the CW laser oscillating section 51 oscillates a CW laser to irradiate the CW laser toward the cell 23 through the optical fiber 20 (step S101). Then, the optical detector 54 detects an amount of reflected light of the CW laser that is reflected by the cell 23 (step S102).

Subsequently, the optical detector 54 examines whether the detected amount of reflected light is larger than the predetermined threshold (step S103), and when the amount of the reflected light is not larger than the threshold (step S103, No), the detection process is continued until the amount of the reflected light becomes greater than the threshold.

When the amount of the reflected light is larger than the threshold (step S103, Yes), the pulse laser oscillating section 50 oscillates a pulse laser to irradiate the pulse laser to the cell 23 through the optical fiber 20 (step S104) to form an opening in the surface of the cell 23.

Then, the pump. 26 applies a pressure to the drug fluid 22 in the drug fluid ejecting nozzle 21 to eject the drug fluid 22 toward the opening to thereby injecting the drug fluid 22 into the cell 23 (step S105). Thereafter, the controller 30 examines whether an instruction for terminating the injection process is received (step S106), and when such an instruction is not received (step S106, No), the processes in the step S101 and steps subsequent thereto are continued to the cells 23 into which the drug fluid 22 are to be injected next.

When the instruction is received (step S106, Yes), the drug fluid injection process is terminated.

The laser is conducted to the surface of the cell 23 using the optical fiber 20 and the drug fluid 22 is injected through the opening formed in the surface of the cell 23 using the drug fluid ejecting nozzle 21. Accordingly, the injection of the drug fluid 22 can be performed at low cost and efficiently regardless of the kinds of the cell 23 and the drug fluid 22 to be introduced as well as the number of times of use of the apparatus or method of the present invention.

The drug fluid 22 is injected into the cell by ejecting the drug fluid 22 to the opening formed in the surface of the cell 23 through the drug fluid ejecting nozzle 21. Accordingly, the injection of the drug fluid 22 can be performed efficiently by providing kinetic energy to the drug fluid 22.

The distance between the laser irradiation port of the optical fiber 20 and the surface of the cell 23 is determined from the intensity of the reflection of the laser conducted to the surface of the cell 23 through the optical fiber 20. Accordingly, the timing in which the laser is irradiated to form an opening in the surface of the cell 23 can be detected with ease.

Figure 8:
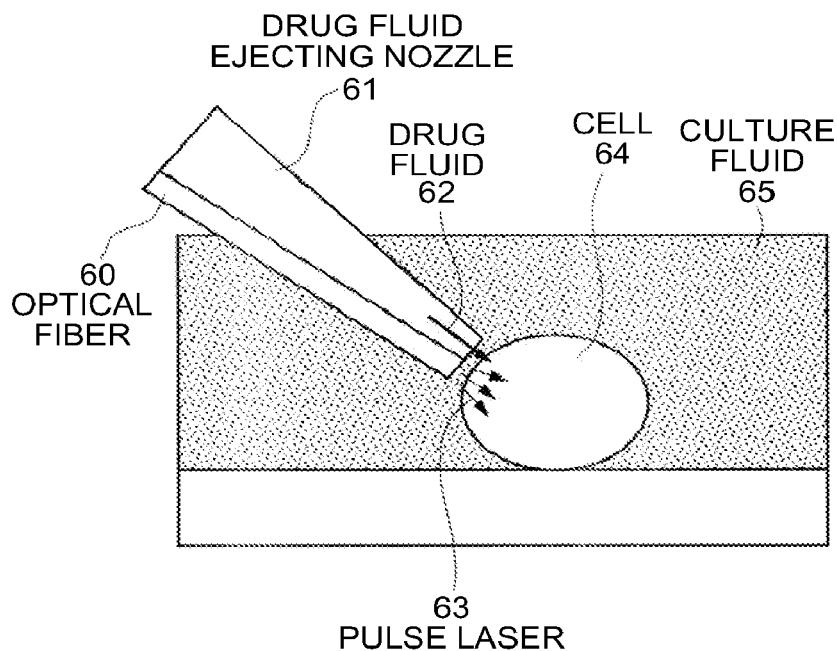
FIG. 8 is a schematic of another exemplary configuration of a drug fluid injecting section that can be used in the drug fluid injecting apparatus shown in FIG. 2.

The optical fiber 20 and the drug fluid ejecting nozzle 21 are provided separately in the configuration shown in FIG. 1. However, as a variation of the drug fluid injecting section explained with respect to FIG. 1, the optical fiber and the drug fluid ejecting nozzle can be integrated. FIG. 8 shows a drug fluid injecting section in which an optical fiber and a drug fluid ejecting nozzle are integrated as one unit.

In the drug fluid injecting section shown in FIG. 8, an optical fiber 60 and a drug fluid ejecting nozzle 61 are integrated by deposition with each other in parallel. The optical fiber 60 conducts a high-power pulse laser 63, which is irradiated for forming an opening in a cell 64 immersed in a culture fluid 65, to the surface of the cell 64. The drug fluid ejecting nozzle 61 ejects a drug fluid 62 into the cell 64 through the opening of the cell 64 formed by the laser 63 conducted through the optical fiber 60.

In this manner, according to the drug fluid injecting section shown in FIG. 8, the laser irradiation port of the optical fiber 60 and the ejecting port of the drug fluid ejecting nozzle that ejects the drug fluid 62 are arranged side by side and integrated as one unit. Accordingly, there is no need to perform the alignment of the irradiation port and the alignment of the ejecting section separately, so that the injection of the drug fluid 62 can be performed efficiently.

In the first embodiment, the optical fiber is arranged outside the drug fluid ejecting nozzle. However, as a second embodiment of the present invention, the optical fiber and the drug fluid ejecting nozzle is integrated as one unit and the optical fiber is arranged inside the drug fluid ejecting nozzle. This configuration permits the injection process to be performed efficiently. Accordingly, in the second embodiment, the case where an optical fiber is arranged inside a drug fluid ejecting nozzle is explained in detail. The configuration of a drug fluid injecting apparatus according to the second embodiment other than the drug fluid injecting section is the same as that shown in FIG. 2, and explanation thereof is omitted.

Figure 9:
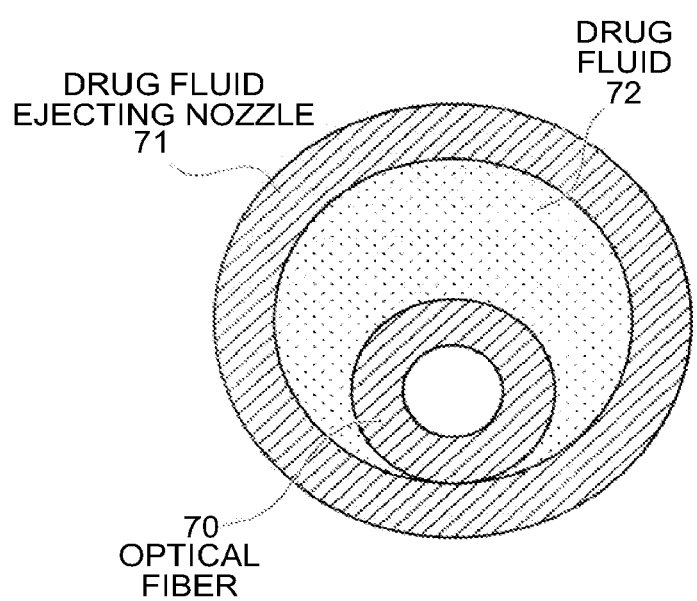
FIG. 9 is a cross-sectional view of a drug fluid injecting section according to a second embodiment of the present invention.

First, the configuration of the drug fluid injecting section according to the second embodiment is explained. FIG. 9 is a cross-sectional view of the drug fluid injecting section according to the second embodiment. The drug fluid injecting section includes an optical fiber 70, which is arranged inside a drug fluid ejecting nozzle 71.

The optical fiber 70 conducts the pulse laser or the CW laser to the surface of a cell or a reflected light of the CW laser to the optical system 29 shown in FIG. 2. The drug fluid ejecting nozzle 71 is a glass tube that ejects the drug fluid 72 toward the opening formed in the surface of the cell by the pulse laser to inject the drug fluid 72 into the cell. The drug fluid 72 is filled in a region sandwiched by an outside of the optical fiber 70 and an inside of the drug fluid ejecting nozzle 71.

Assuming the size of the cell to be about 15 micrometers (μm) and the size of the cell nucleus to be about 1 μm to about 2 μm, appropriate diameter of the drug fluid ejecting nozzle 71 is about 5 μm to about 10 μm, and that of the optical fiber 70 is about 3 μm to about 5 μm.

Figure 10:
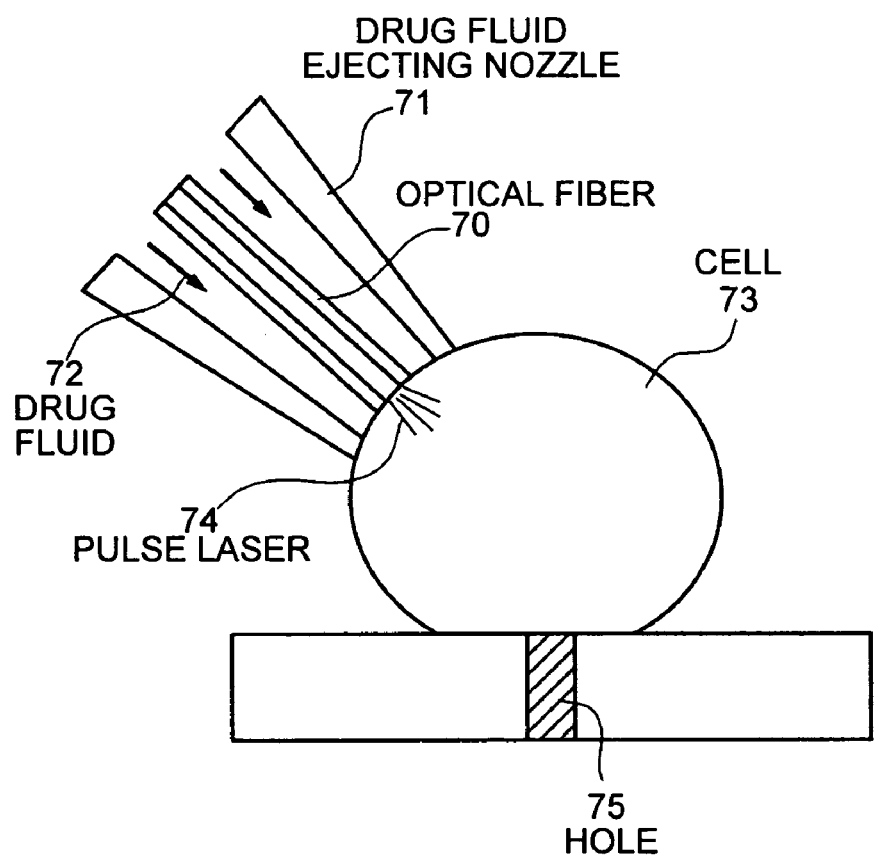
FIG. 10 is a schematic for explaining a method of injecting a drug fluid using the drug fluid injecting section shown in FIG. 9.

FIG. 10 is a schematic for explaining a method for injecting the drug fluid 72 using the drug fluid injecting section shown in FIG. 9. It is common to immerse a cell 73 in a culture fluid, however, the culture fluid is not shown in FIG. 10.

When the tip of the optical fiber 70 contacts the cell 73, a pulse laser 74 is irradiated from the optical fiber 70. Then, when the surface temperature of the cell membrane increases due to the irradiation of the pulse laser 74, a portion of the cell membrane is broken and the drug fluid 72 ejected by the drug fluid ejecting nozzle flows into the cell 73 immediately before the irradiation of the pulse laser 74 or simultaneously with the irradiation of the pulse laser 74.

Figure 21:
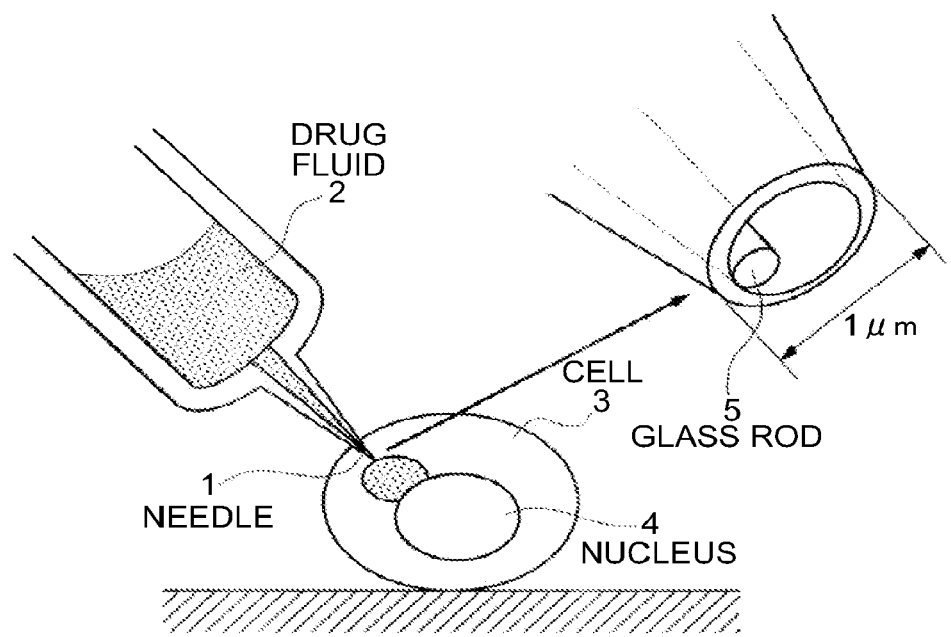
FIG. 21 is a schematic for explaining the conventional microinjection method.
Figure 22:
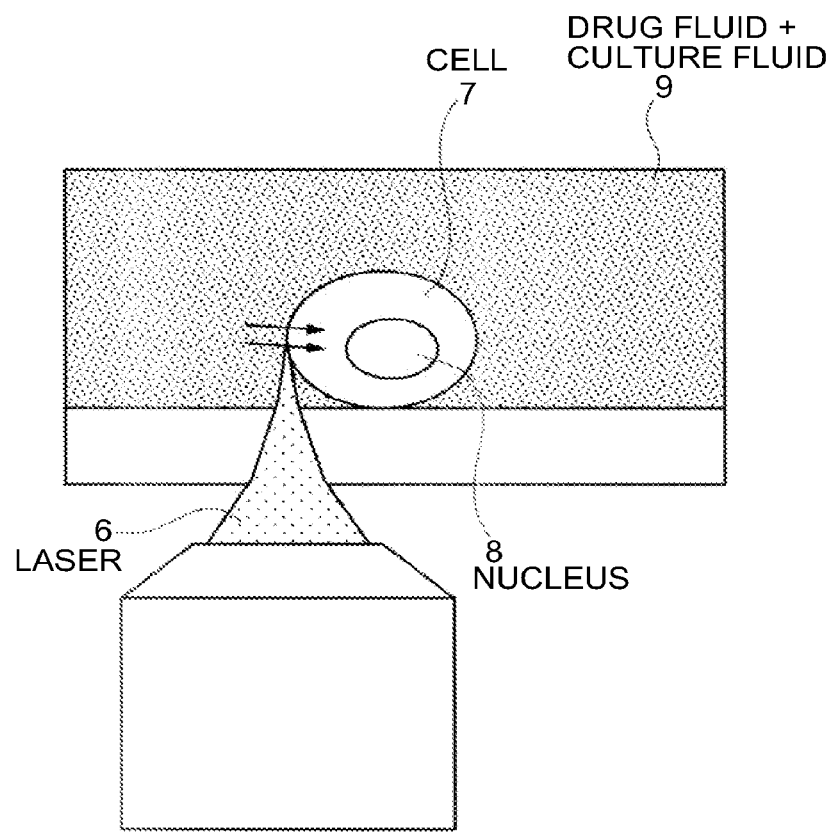
FIG. 22 is a schematic for explaining a conventional laser injection method.

There is a possibility that the cell 73 is pushed out by the pressure of the culture fluid when the tip of the optical fiber 70 approaches, and the tip of the drug fluid injecting section and the cell 73 do not contact, so that it is desirable that the culture fluid be sucked through a hole 75 to immobilize the cell 73. By arranging the optical fiber 70 in the inside of the drug fluid ejecting nozzle 71, the optical fiber 70 can as well be caused to play the role of the rod explained with respect to FIG. 21.

Figure 11:
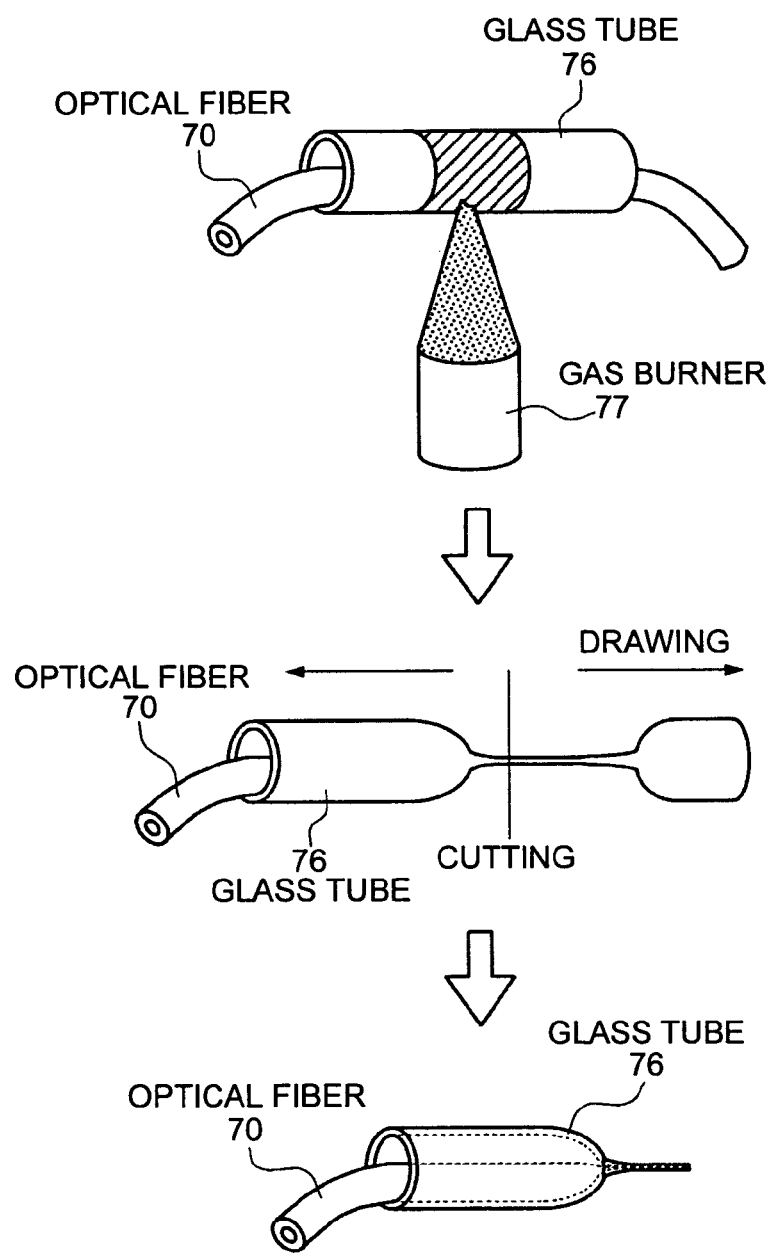
FIG. 11 is a schematic for explaining a method of manufacturing the drug fluid injecting section shown in FIG. 9.

FIG. 11 is a schematic for explaining a method of manufacturing the drug fluid injecting section shown in FIG. 9. When manufacturing the drug fluid injecting section, first the optical fiber 70 is placed in a glass tube 76 and the glass tube 76 is heated to melt by means of a gas burner 77 or the like. The glass tube 76 is then drawn at a stroke to elongate the molten portion of the glass tube 76, and the elongated portion is cut to form a drug fluid injecting section. This portion of the glass tube 76 corresponds to a portion that serves as the drug fluid ejecting nozzle 71.

Figure 12:
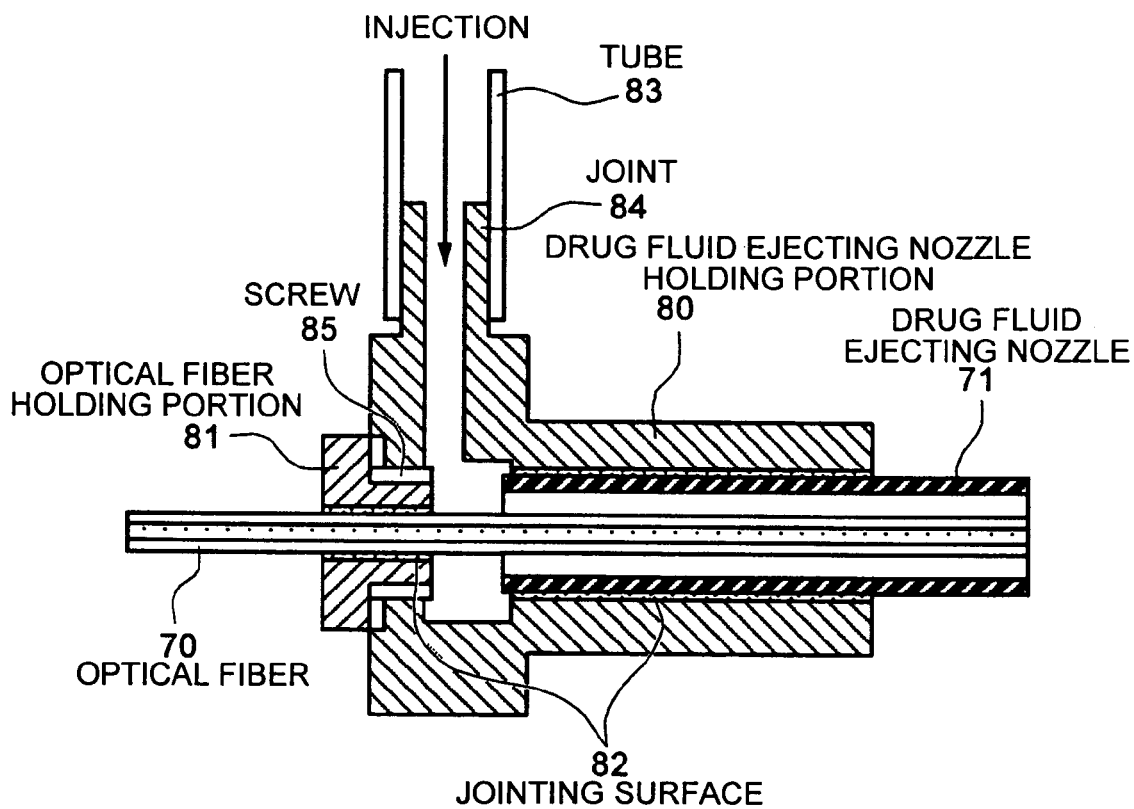
FIG. 12 is a cross-sectional view of a drug supplying section that supplies a drug fluid to the drug fluid injecting section shown in FIG. 9.

A drug fluid supplying section that supplies a drug fluid to the drug fluid injecting section shown in FIG. 9 is explained. FIG. 12 is a cross-sectional view of the drug fluid supplying section that supplies a drug fluid to the drug fluid injecting section shown in FIG. 9. The drug fluid supplying section includes a drug fluid ejecting nozzle holding portion 80 and an optical fiber holding portion 81.

The drug fluid ejecting nozzle holding portion 80 and the optical fiber holding portion 81, which are integrated with a screw 85, hold the drug fluid ejecting nozzle 71 and the optical fiber 70 bonded on a jointing surfaces 82 to separate a space into which the drug fluid is injected and a space through which the laser is passed. The drug fluid ejecting nozzle holding portion 80 has a joint 84 for connecting a tube 83 for injecting the drug fluid.

The optical fiber 70 that conducts the laser to the surface of the cell 73 is arranged in the inside of the drug fluid ejecting nozzle 71 that injects the drug fluid 72 into the cell 73. Accordingly, the optical fiber 70 and the drug fluid ejecting nozzle 71 can be integrated and the drug fluid injecting process can be performed efficiently.

Although the drug fluid injecting section is configured in such a manner that the position of the tip of the optical fiber 70 and the position of the tip of the drug fluid ejecting nozzle 71 coincide with each other as shown in FIG. 10, the drug fluid injecting section can also be configured in such a manner that the position of the tip of the optical fiber 70 is retreated from the tip of the drug fluid ejecting nozzle 71 to allow the drug fluid to easily enter the opening formed by the irradiation of the laser.

Figure 13:
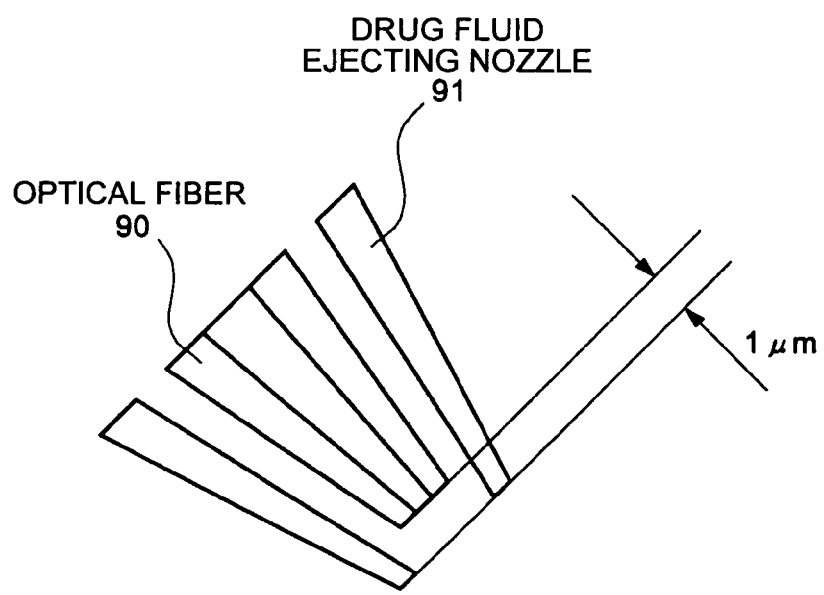
FIG. 13 is a schematic of another drug fluid injecting section according to the second embodiment.

FIG. 13 is a schematic of a drug fluid injecting section in which the position of the tip of an optical fiber 90 is retreated from the position of the tip of a drug fluid ejecting nozzle 91. In this drug fluid injecting section, the position of the tip of the optical fiber 90 is retreated inward from the position of the tip of the drug fluid ejecting nozzle 91. An appropriate amount of this retreat is about 1 μm.

Figure 14:
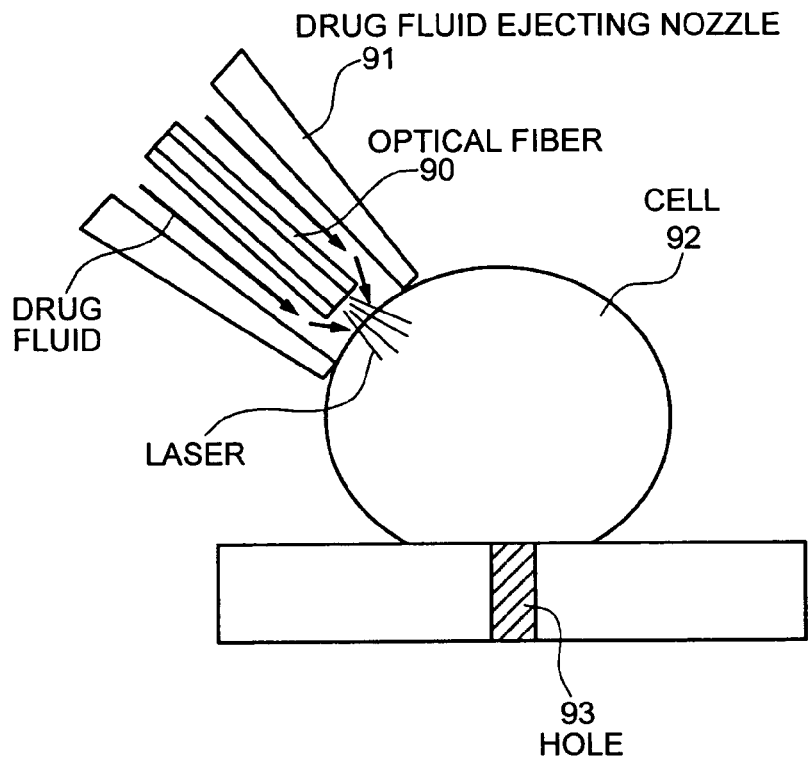
FIG. 14 is a schematic for explaining a method for injecting a drug fluid using the drug fluid injecting section shown in FIG. 13.

FIG. 14 is a schematic for explaining a method for injecting a drug fluid using the drug fluid injecting section shown in FIG. 13. Sine the position of the tip of the optical fiber 90 is retreated inward from the position of the tip of the drug fluid ejecting nozzle 91 as shown in FIG. 14, a gap is formed between the tip of the optical fiber 90 and a cell 92.

According to the configuration shown in FIG. 13, the optical fiber 90 is arranged in such a manner that the position of the irradiation port of the optical fiber 90 is retreated from the position of the ejecting port for ejecting the drug fluid of the drug fluid ejecting nozzle 91. Accordingly, the drug fluid can be injected into the cell 92 more easily.

There is a possibility that the cell 92 moves due to the pressure of the culture fluid when the tip of the optical fiber 90 approaches. Therefore, it is desirable that the culture fluid be sucked through a hole 93 that is formed in, for example, a Petri dish in which the cell 92 is charged to immobilize the cell 92.

In the second embodiment, the cell is immobilized by sucking the culture fluid from a hole formed in, for example, a Petri dish for mounting. However, the cell can be immobilized by forming a sucking portion for sucking the culture fluid in the drug fluid injecting section and sucking the culture fluid therethrough to trap the cell.

This prevents the cell from being moved by the impact upon irradiating the laser. By moving the tip of the drug fluid injecting section while sucking the culture fluid in the Petri dish, the drug fluid injecting section can be moved without disturbing the motion of the culture fluid in the Petri dish.

Accordingly, in the third embodiment, the case where a liquid sucking tube is formed in the drug fluid injecting section and the culture fluid is sucked therethrough to immobilize the cell is explained. The other configuration of a drug fluid injecting apparatus according to the third embodiment is the same as that shown in FIG. 2, so that explanation thereof is omitted.

Figure 15:
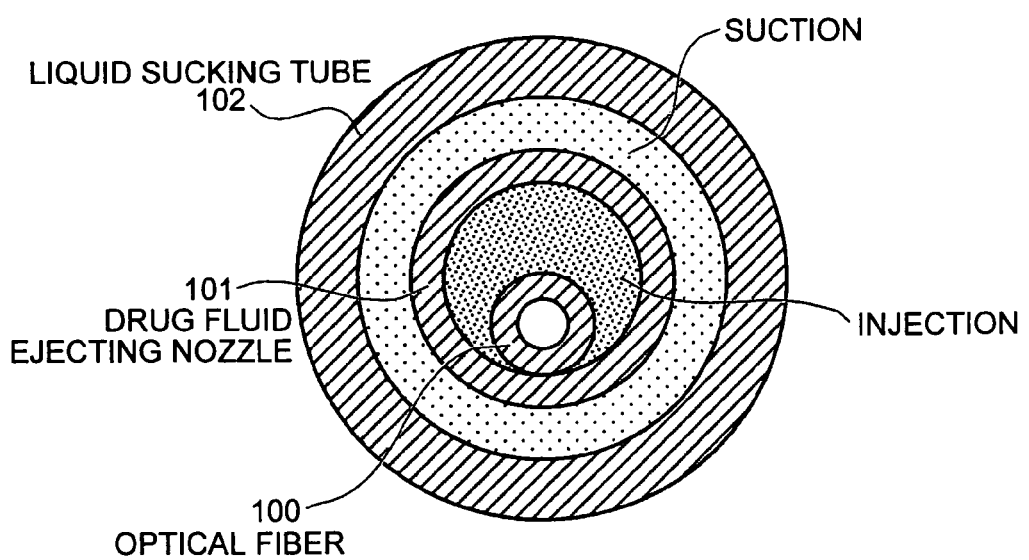
FIG. 15 is a cross-sectional view of a drug fluid injecting section according to a third embodiment of the present invention.

First, the configuration of the drug fluid injecting section according to the third embodiment is explained. FIG. 15 is a cross-sectional view of the drug fluid injecting section according to the third embodiment. The drug fluid injecting section includes an optical fiber 100, which is arranged in the inside of a drug fluid ejecting nozzle 101. The drug fluid ejecting nozzle 101 is arranged in the inside of a liquid sucking tube 102.

The optical fiber 100 conducts the pulse laser or the CW laser to a surface of a cell or a reflected light of the CW laser to the optical system 29 shown in FIG. 2. The drug fluid ejecting nozzle 101 is a glass tube that ejects the drug fluid toward the opening formed in the surface of the cell by the pulse laser to inject the drug fluid into the cell. The drug fluid is filled in a region sandwiched by an outside of the optical fiber 100 and an inside of the drug fluid ejecting nozzle 101.

The liquid sucking tube 102 is a glass tube that sucks the culture fluid stored in, for example, a Petri dish containing a cell. The liquid sucking tube 102 is connected with the pump 26 shown in FIG. 2, and the culture fluid is sucked from the region sandwiched by the outside of the drug fluid ejecting nozzle 101 and the inside of the liquid sucking tube 102.

Figure 16:
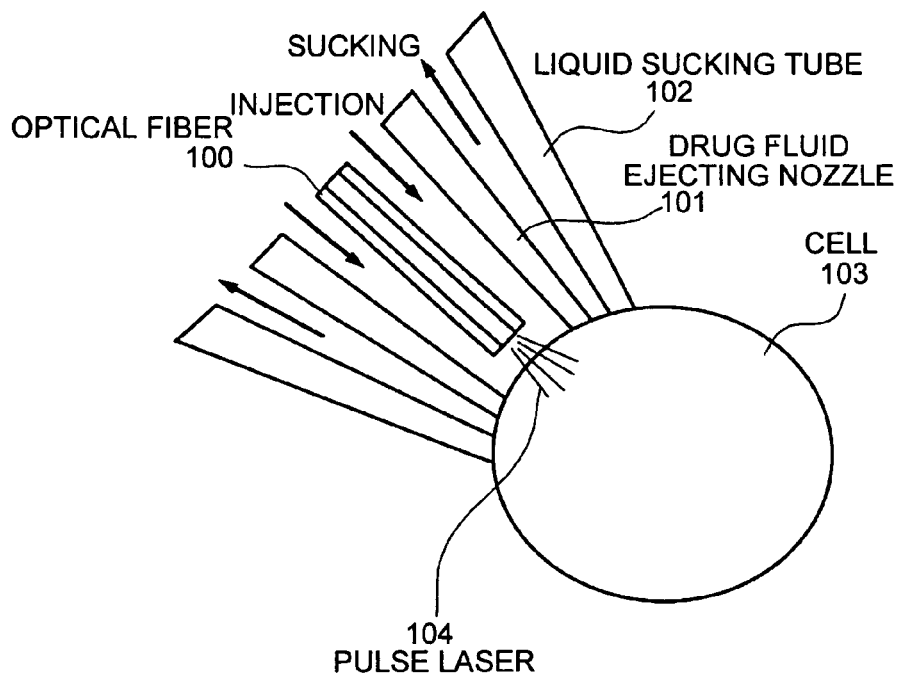
FIG. 16 is a schematic for explaining a method of injecting a drug fluid using the drug fluid injecting section shown in FIG. 15.

FIG. 16 is a schematic for explaining a method of injecting a drug fluid using the drug fluid injecting section shown in FIG. 15. It is common to immerse a cell 103 in a culture fluid, however, the culture fluid is shown in FIG. 16.

When the drug fluid injecting section approaches the cell 103, the culture fluid in the Petri dish is sucked from the region between the liquid sucking tube 102 and the drug fluid ejecting nozzle 101, and the cell 103 is sucked toward the tip of the drug fluid injecting section.

When the tip of the optical fiber 100 approaches the cell 103, a pulse laser 104 is irradiated from the optical fiber 100. Thereafter, when the surface temperature of the cell membrane increases due to the irradiation of the pulse laser 104, a portion of the cell membrane is broken and the drug fluid ejected by the drug fluid ejecting nozzle 101 flows into the cell 103.

Figure 17:
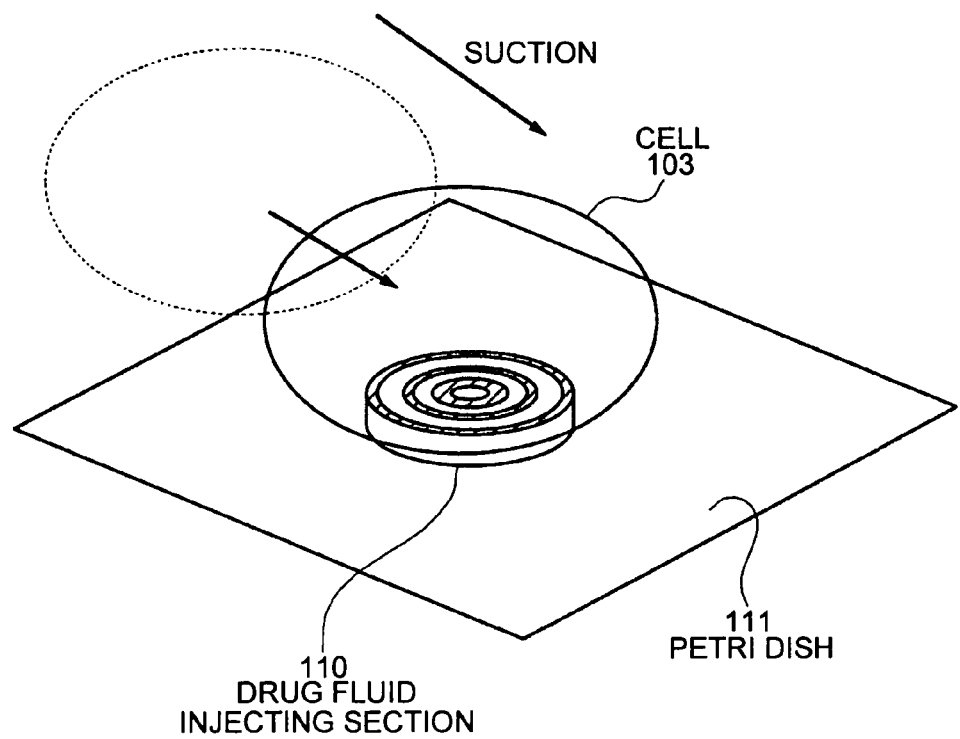
FIG. 17 is a perspective of a drug fluid injecting section formed on the bottom of a Petri dish.

A drug fluid injecting section can be formed in the bottom of the Petri dish 111 as shown in FIG. 17. When the culture fluid in the Petri dish 111 is sucked by a drug fluid injecting section 110, the cell 103 is trapped in the drug fluid injecting section 110. It is desirable that a flow of the culture fluid be formed in the Petri dish 111, so that the cell 103 is readily changed and the cell 103 is trapped in the drug fluid injecting section 110.

Figure 18:
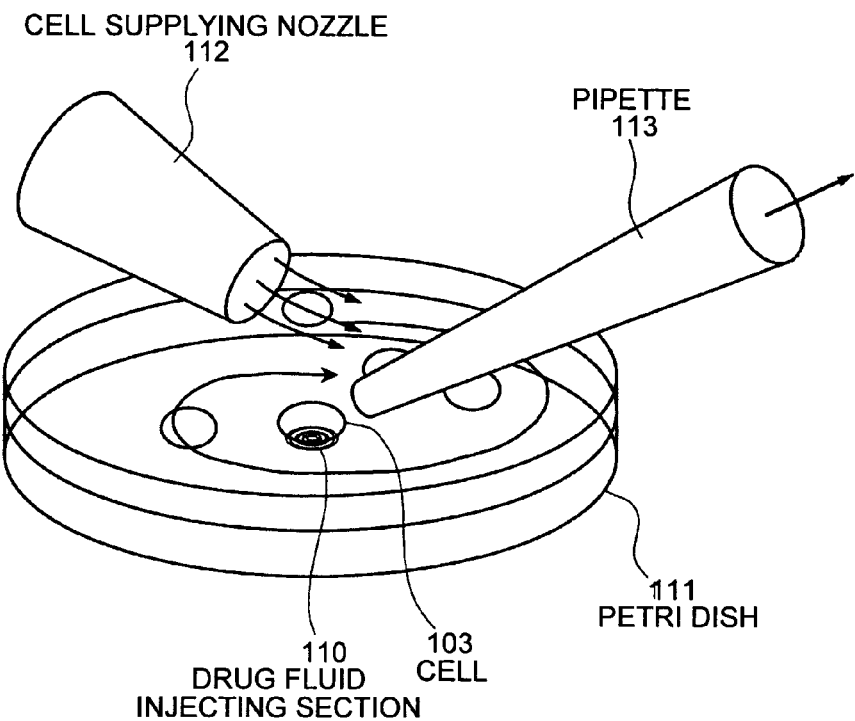
FIG. 18 is a schematic for explaining a method for generating a flow of a culture fluid containing a cell 103 in the Petri dish.

FIG. 18 is a schematic for explaining a method for generating a flow of a culture fluid, which contains the cell 103, in the Petri dish 111. A swirl of the culture fluid is formed in the Petri dish 111 by ejecting the culture fluid containing the cells 103 from a cell supplying nozzle 112 toward a fringe of the Petri dish 111.

This causes the cells 103, which is slightly heavier than the culture fluid, to gather together in the center of the bottom of the Petri dish 111, so that the cells 103 can be trapped with ease. The cells 103 into which the drug fluid has been injected are taken out and transferred to a Petri dish (not shown) for cultivation.

Figure 19:
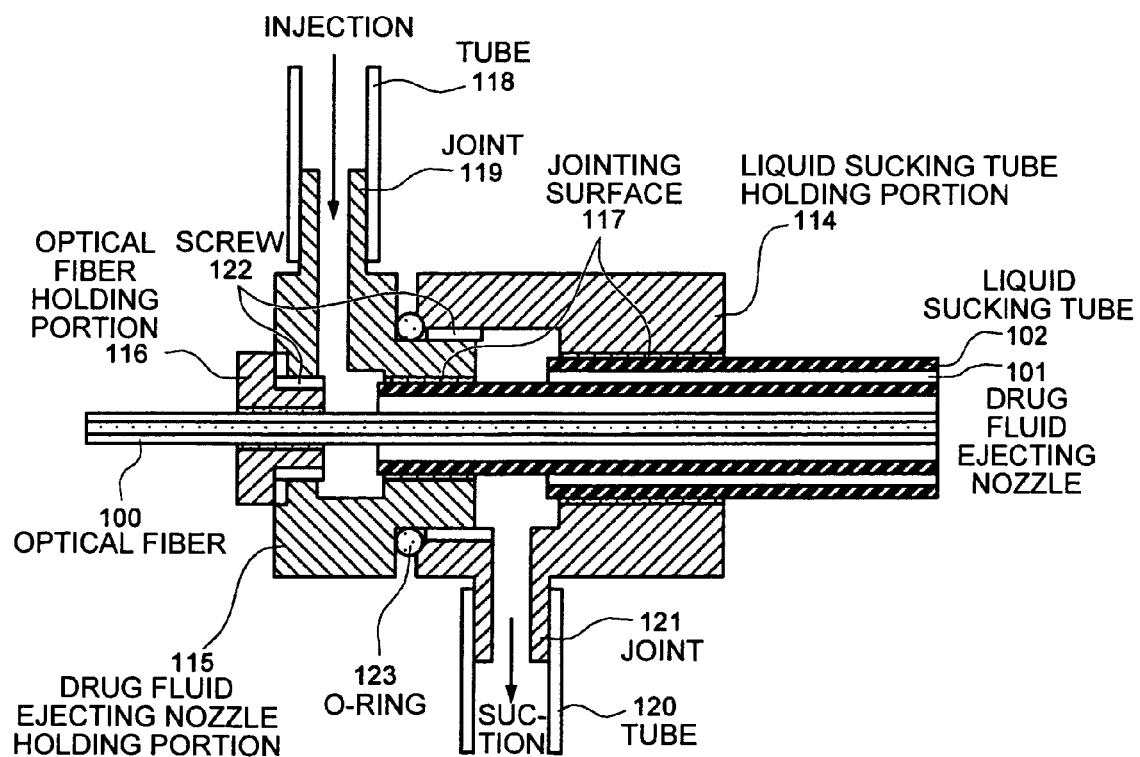
FIG. 19 is a cross-sectional view of a drug fluid supplying section that supplies the drug fluid to the drug fluid injecting section shown in FIG. 15.

Then, a drug fluid supplying section that supplies a drug fluid to the drug fluid injecting section shown in FIG. 15 is explained. FIG. 19 is a cross-sectional view of the drug fluid supplying section that supplies the drug fluid to the drug fluid injecting section shown in FIG. 15. The drug fluid supplying section includes a liquid sucking tube holding portion 114, a drug fluid ejecting nozzle holding portion 115, and an optical fiber holding portion 116.

The liquid sucking tube holding portion 114, the drug fluid ejecting nozzle holding portion 115, and the optical fiber holding portion 116 are integrated to each other with a screw 122 and an O-ring 123 to bond and hold the liquid sucking tube 102, the drug fluid ejecting nozzle 101, and the optical fiber 100 on the jointing surfaces 117, respectively, to separate a space from which the culture fluid is sucked, a space into which the drug fluid is injected, and a space through which the laser is passed, respectively.

The liquid sucking tube holding portion 114 has a joint 121 that connects a tube 120 for sucking the culture fluid. The drug fluid ejecting nozzle holding portion 115 has a joint 119 that connects a tube 118.

Figure 20:
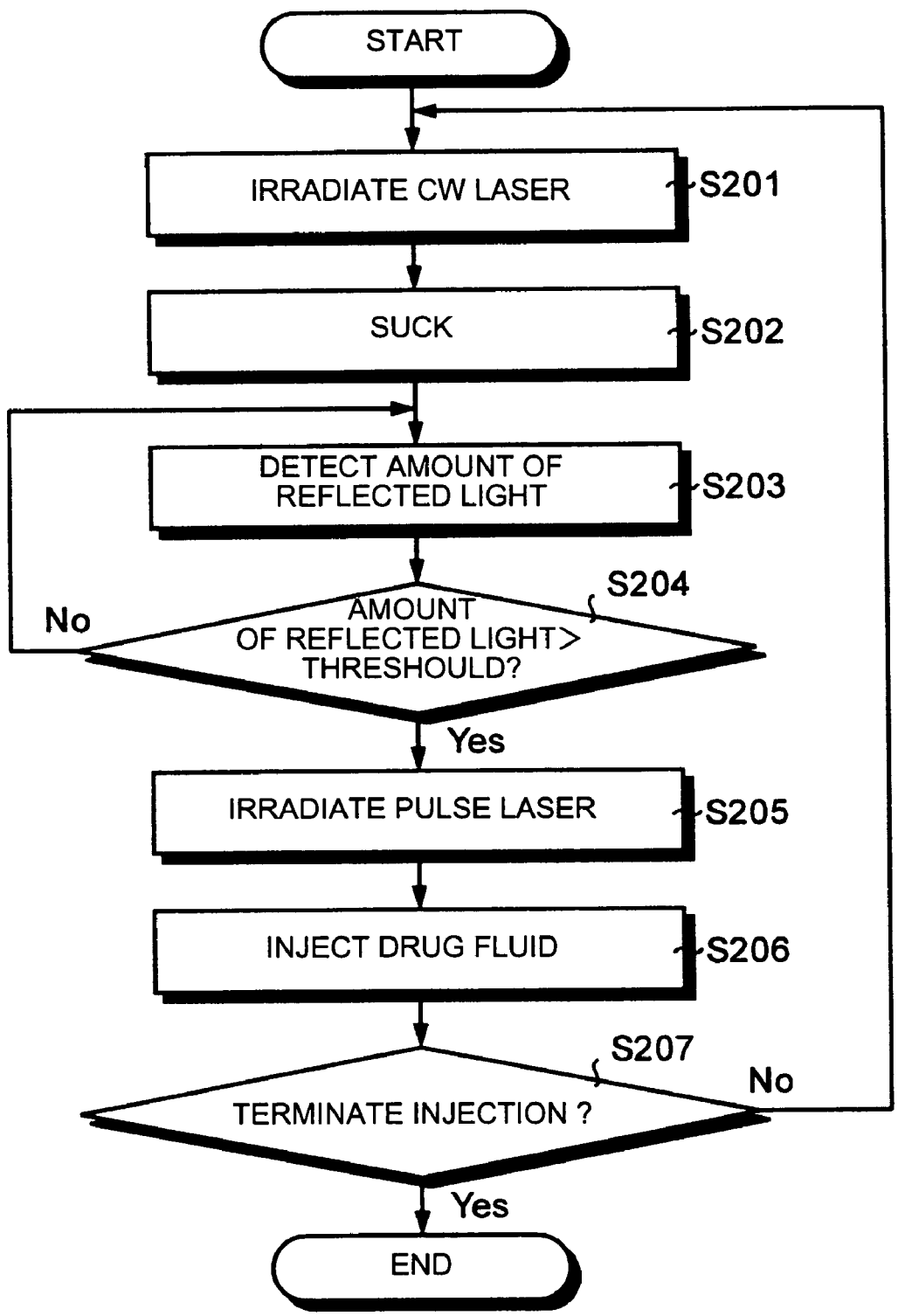
FIG. 20 is a flowchart of a drug fluid injecting process procedure performed by a drug fluid injecting apparatus according to the third embodiment.

Then, a drug fluid injecting process performed by the drug fluid injecting apparatus according to the third embodiment is explained. FIG. 20 is a flowchart of the drug fluid injecting process.

First, the CW laser oscillating section 51 oscillates a CW laser to irradiate the CW laser toward the cell 103 through the optical fiber 100 (step S201). Then, the pump 26 starts suck the culture fluid through the liquid sucking tube 102 (step S202) to trap the cell 103 in the tip of the drug fluid injecting section. Subsequently, the optical detector 54 detects an amount of the reflected light of the CW laser that is reflected by the cell 103 (step S203).

Thereafter, the optical detector 54 examines whether the detected amount of the reflected light is larger than the predetermined threshold (step S204), and when the amount of the reflected light is not larger than the threshold (step S204, No), the detection process is continued until the amount of the reflected light becomes greater than the threshold.

When the amount of the reflected light is larger than the threshold (step S204, Yes), the pulse laser oscillating section 50 oscillates a pulse laser to irradiate the pulse laser to the cell 103 through the optical fiber 20 (step S205) to form an opening in the surface of the cell 103.

Then, the pump 26 applies a pressure to the drug fluid in the drug fluid ejecting nozzle 101 to eject the drug fluid toward the opening to thereby inject the drug fluid into the cell 103 (step S206). Thereafter, the controller 30 examines whether an instruction for terminating the injection process is received (step S207), and when such an instruction is not received (step S207, No), the processes in the step S201 and subsequent thereto are continued to the cells 103 into which the drug fluid are to be injected.

When the instruction is received (step S207, Yes), the drug fluid injection process is terminated.

The cells 103 are adsorbed by sucking the culture fluid around the cells 103 through the sucking port of the liquid sucking tube 102 formed around the drug fluid ejecting port of the drug fluid ejecting nozzle 101. Accordingly, the drug fluid injecting process can be performed with ease while preventing the cells 103 from moving.

The drug fluid injecting section 110 that injects the drug fluid into the cells 103 is arranged in the Petri dish 111 containing the cells 103, the immobilization of the cells 103 and the drug fluid injecting process can be performed efficiently.

According to the present invention, a configuration is adopted in which a laser is led onto the surface of a cell to form an opening and a substance is injected through the opening, so that the invention has an effect that the injection of the substance can be performed at low cost and efficiently regardless of the kinds of the cells and the substance to be introduced as well as the number of times of use of the needle.

According to the present invention, the substance is injected into the cells by ejecting the substance into the opening, in other words, kinetic energy is applied to the substance. Accordingly, the substance can be injected into the cell efficiently.

According to the present invention, the irradiation port for irradiating the laser and the ejection port for ejecting the substance are arranged side by side and integrated. Accordingly, the present invention has an effect that the irradiation port and the ejection port do not have to be aligned separately. This enables efficient injection of the substance into the cells.

According to the present invention, the light conducting unit that conducts the laser to the cell surface is placed in the inside of the substance injecting unit. Accordingly, the present invention has an effect that the light conducting unit and the substance injecting unit can be integrated to enable one to perform the substance injecting process efficiently.

According to the present invention, the irradiation port is placed at a place that is hollow with respect to the position of the ejection port that ejects the substance. Accordingly, the present invention has an effect that the substance can be injected into the cells with ease.

According to the present invention, the fluid around the cell is sucked through the suction hole formed around the ejection port that ejects the substance to trap the cell on the suction hole. Accordingly, the present invention has an effect that the substance injection process can be performed with ease while preventing the migration of the cell.

According to the present invention, the light conducting unit that conducts the laser onto the cell surface and the substance injecting unit that injects the substance into the cell are placed in the housing unit that houses the cell. Accordingly, the present invention has an effect that the fixing of the cell and the substance injecting process can be performed efficiently.

According to the present invention, the distance between the irradiation port for the laser and the surface of the cell is judged based on the intensity of the reflection of the laser conducted to the cell surface. Accordingly, the present invention has an effect that the timing of irradiation of the laser onto the surface of the cell to form an opening in the surface of the cell can be detected with ease.

According to the present invention, the laser is irradiated onto the surface of the cell by means of the light conducting unit that conducts the laser onto the cell surface, and the substance is injected into the cell through the opening formed by the irradiation of the laser onto the surface of the cell. Accordingly, the present invention has an effect that the injection of the substance into cells can be performed at low cost and efficiently regardless of the kinds of the cell and the substance to be introduced as well as the number of times of use of the apparatus or method.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. An apparatus for injecting a substance into a cell, comprising:
   a light conducting unit to conduct a laser beam to a surface of a cell to form an opening in the surface;
   a substance injecting unit to insert the substance into the cell through the opening; and
   a sucking port to suck the cell and to immobilize the cell while the substance is being inserted in the cell, wherein
   the light conducting unit is arranged inside the substance injecting unit, and the sucking port is formed around the substance injecting unit.

2. The apparatus according to claim 1, wherein
the substance injecting unit inserts the substance in the cell by ejecting the substance in the opening.

3. The apparatus according to claim 2, wherein
the light conducting unit includes an irradiation port to direct the laser beam to the surface of the cell, the substance injecting unit includes an ejecting port to insert the substance into the cell, and the irradiation port and the ejecting port are integrated in one unit.

4. The apparatus according to claim 1, wherein
the light conducting unit includes an irradiation port to direct the laser beam to the surface of the cell, the substance injecting unit includes an ejecting port to insert the substance into the cell, and a tip of the irradiation port retreats with respect to a tip of the ejecting port.

5. The apparatus according to claim 1, wherein the light conducting unit and the substance injecting unit are arranged in a housing unit that houses the cells.

6. The apparatus according to claim 1, wherein the light conducting unit includes an irradiation port to direct the laser beam to the surface of the cell, and
the apparatus further comprises
   a measuring unit to measure an intensity of laser beam reflected from the surface of the cell; and
   a determining unit to determine a distance between the irradiation port and the surface of the cell based on the intensity measured.

7. A method for injecting a substance into a cell, comprising:
   irradiating a surface of a cell with a laser beam to form an opening in the surface of the cell using a light conducting unit that conducts the laser beam to the surface of the cell;
   sucking the cell using a sucking port to immobilize the cell while the substance is being inserted in the cell; and
   inserting the substance into the cell through the opening using a substance injecting unit wherein the light conducting unit is arranged inside the substance injecting unit, and the sucking port is formed around the substance injecting unit.

* * * * *